United States Patent [19]

Lawhon et al.

[11] Patent Number: 5,407,071

[45] Date of Patent: * Apr. 18, 1995

[54] PACKAGE FOR AN ELONGATED FLEXIBLE FIBER AND METHOD OF USE

[75] Inventors: Harvey A. Lawhon, Forest Hill; William W. Gardetto, Bedford, both of Tex.

[73] Assignees: MyriadLase, Inc., Forest Hill; MicroBioMed Corporation, Dallas, both of Tex.

[*] Notice: The portion of the term of this patent subsequent to Nov. 23, 2010 has been disclaimed.

[21] Appl. No.: 103,578

[22] Filed: Aug. 9, 1993

Related U.S. Application Data

[63] Continuation of Ser. No. 880,136, May 7, 1992, Pat. No. 5,263,585.

[51] Int. Cl.⁶ .................. B65D 85/04; A61B 17/06; B65H 18/78
[52] U.S. Cl. ................... 206/388; 206/63.3; 206/408; 242/129; 242/159
[58] Field of Search .......... 206/63.3, 227, 303, 206/388, 408, 409; 242/129, 159, 164, 170, 54 R, 107.1, 85.1, 132, 146, 137, 138

[56] References Cited

U.S. PATENT DOCUMENTS

| | | |
|---|---|---|
| 2,533,495 | 12/1950 | Moffett . |
| 2,615,565 | 10/1952 | Bower et al. .............. 206/63.3 |
| 3,127,992 | 4/1964 | Horine ..................... 206/63.3 |
| 3,138,309 | 6/1964 | Hulterstrum . |
| 3,301,393 | 1/1967 | Regan, Jr. et al. . |
| 3,338,401 | 8/1967 | Regan, Jr. . |
| 3,495,703 | 2/1970 | Calabrese . |
| 3,545,608 | 12/1970 | Berger et al. ............. 206/63.3 |
| 3,648,949 | 3/1972 | Berger et al. ............. 242/159 |
| 3,731,793 | 5/1973 | Hagel ...................... 206/63.3 |
| 3,752,303 | 8/1973 | Foster ..................... 206/408 |
| 4,685,636 | 8/1987 | Eaton ...................... 242/129 |
| 4,974,789 | 12/1990 | Milbun .................... 242/159 |
| 5,263,585 | 11/1993 | Lawhon et al. ........... 206/388 |

OTHER PUBLICATIONS

Exhibits A1, A2, B1 and B2-Polaroid Photographs (Provider patent application Ser. No. 07/880136).

Primary Examiner—Bryon P. Gehman
Attorney, Agent, or Firm—Dougherty, Hessin, Beavers & Gilbert

[57] ABSTRACT

A package for an elongated flexible fiber. The package comprises a pair of package portions which define a fiber receiving cavity therein. Lips around the perimeter of the package allow a fiber to be wrapped thereon and passed between the lips into the fiber receiving cavity. Each package portion defines a fiber end receiving cavity therein, each fiber end receiving cavity being adapted for receiving an end of the fiber. Each fiber receiving cavity may be deflected away from the opposite package portion, thereby freeing the corresponding end of the fiber. The natural spring action of the elastically flexible fiber will cause the end of the fiber to pop radially outwardly from the package. Terminals, operating tips and other devices may be attached to the ends of the fibers. After both ends of the fiber have been thus freed, the package may be repositioned along the length of extended fiber by simply rolling it so that one section of the fiber is rewound into the package, and the other section is further unwound therefrom. The invention is particularly adapted for use with light transmitting fibers, such as used with surgical lasers in medical environments. The package and fiber may be easily sterilized prior to use, and after use the fiber may be rewound into the package for easy disposal as biomedical waste. In non-medical areas, such as light transmitting fibers in the communication industry, the package is reusable.

20 Claims, 3 Drawing Sheets

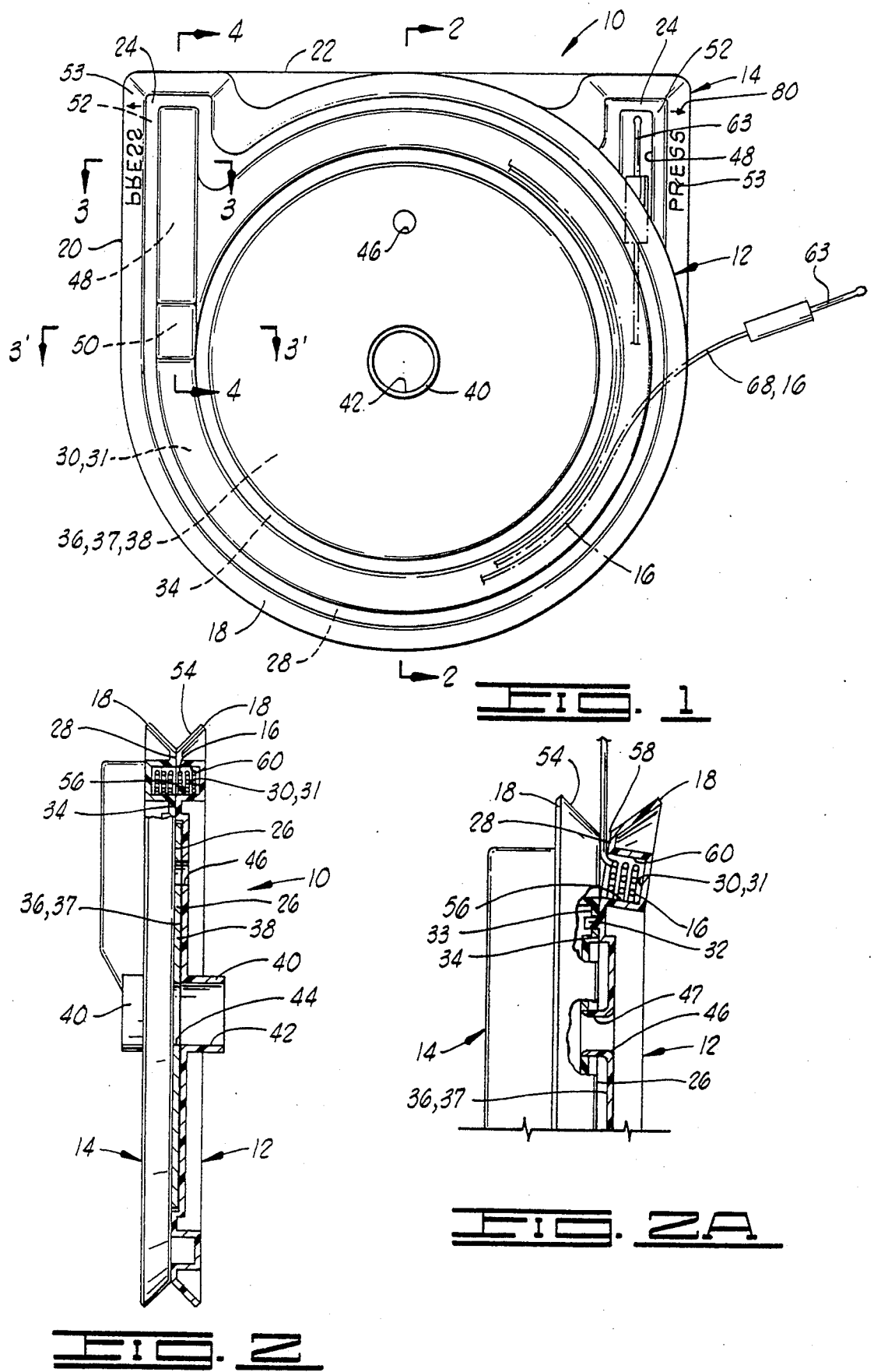

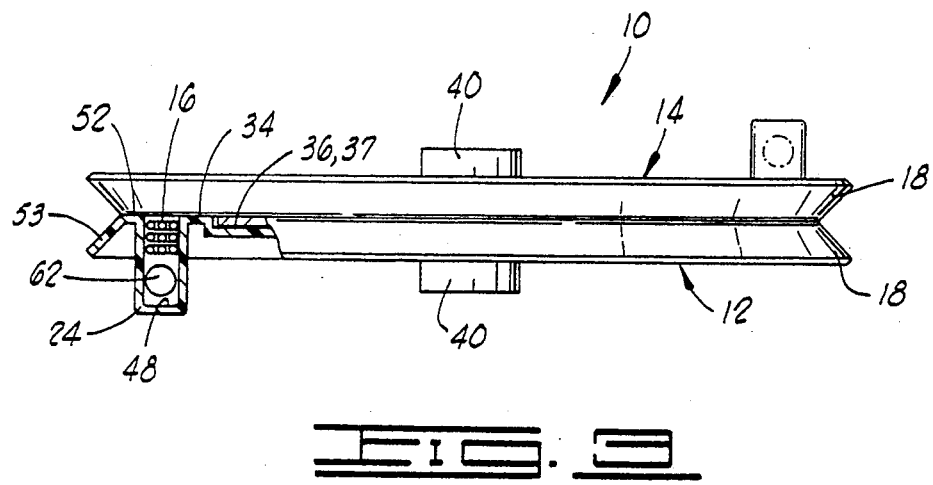
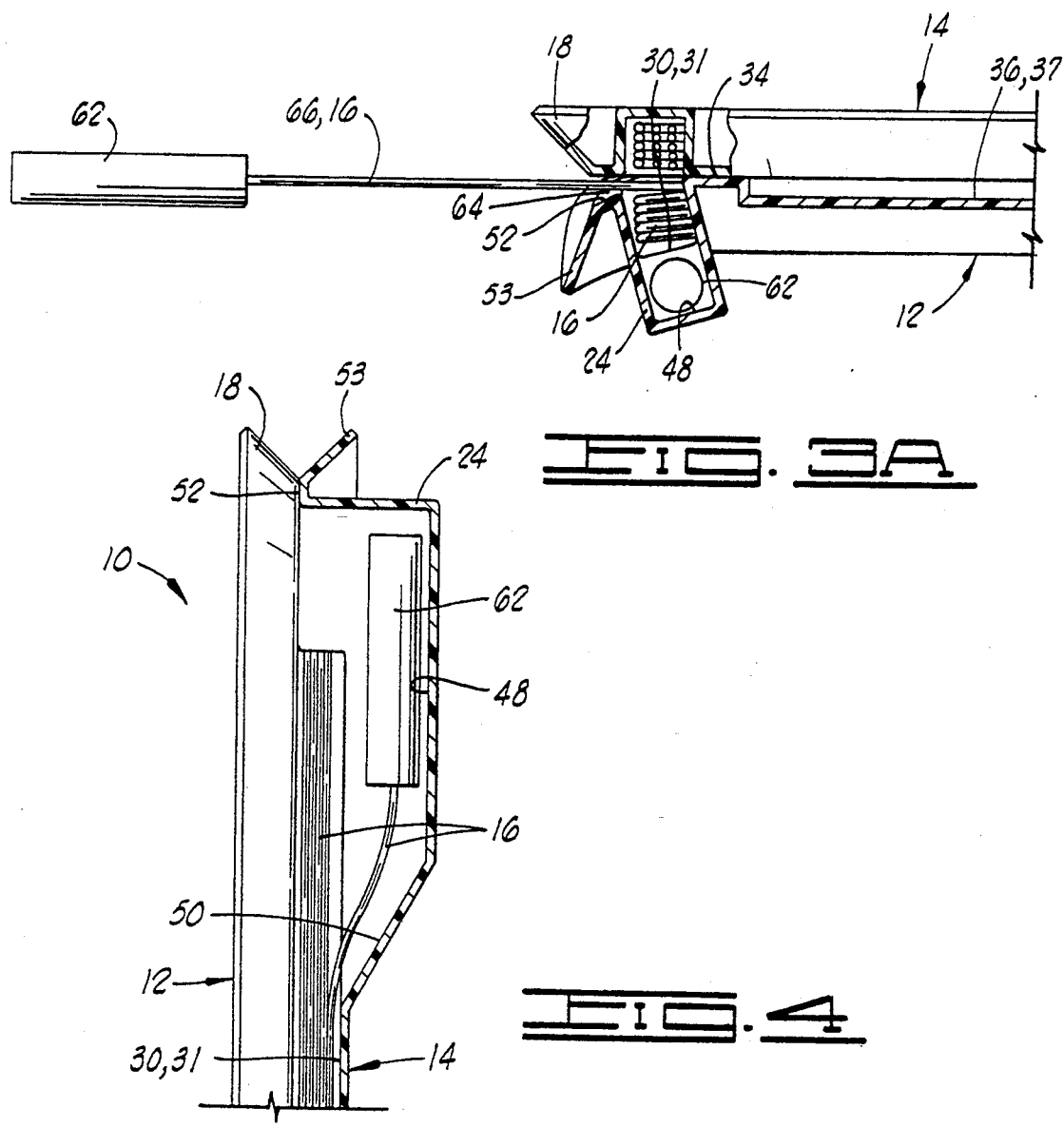

PACKAGE FOR AN ELONGATED FLEXIBLE FIBER AND METHOD OF USE

This is a continuation of application Ser. No. 07/880,136 filed on May 7, 1992, now U.S. Pat. No. 5,263,585.

BACKGROUND OF THE INVENTION

1. Field of the Invention

The present invention relates to a package for an elongated flexible fiber, and more particularly, to a reusable package which provides quick access to the ends of the fiber and which allows easy winding and unwinding of the fiber from the package. Specifically, but not by way of limitation, the invention relates to a package for a light-transmitting fiber such as used with a surgical laser.

2. Description of the Prior Art

The handling and storage of elastically flexible fibers present certain problems. For the purposes of this disclosure, an elastically flexible fiber is one which can be rolled into a coil but which has a degree of natural spring action which tends to substantially return the fiber to its original, elongated configuration. Thus, with such fibers, it is necessary to provide a means for retaining the fiber so that it does not uncoil or unspool itself.

Not only is there a problem in retaining the fiber on whatever spool on which it is wound, it is desirable in some cases that each end of the fiber be easily unwound so that a desired length of fiber may extend from the spool to each end. In doing this, it is frequently desirable to maintain the rest of the fiber on the spool. In other words, there are occasions when both ends of the fiber may be used, but unwinding the entire fiber is undesirable because it may result in a tangled coil of fiber which could obstruct proper use of the fiber.

One area in which such elastically flexible fibers are found is that of fiber-optics which utilize flexibly elongated light-transmitting fibers. These are used in many application, such as the communications industry. Of particular interest is the area of medical technology which involves application of light energy, typically laser light energy, to a site in the patient's body to alter, remove or destroy tissue in the patient's body. This may be done with bare fibers or with fibers having a tip on one end. The other end of the fiber typically has a connector for connecting to the light source. Particular needs in the medical area are that the fiber package be maintained in a sterile condition prior to its use, be easily handled and accessed during use, and be easily adapted for proper disposal as biomedical waste after use.

One prior art package for light transmitting fibers used for medical lasers includes a pair of plastic package portions which are connected together around the perimeter thereof. There are openings in the package through which the ends of the fiber extend. A holding means is provided for holding protective sleeves positioned on the terminal end and the surgical operating tip end. Once the fiber has been pulled from the package, the package is not easily repositioned along the length of the fiber, nor is it easily reinserted into the package for simple disposal.

The present invention solves these problems by providing a container or package into which a length of fiber may be wound and which has cavities therein for receiving each end of the fiber, including fibers with terminals or other devices such as surgical operating tips attached to the ends. The package and fiber may be sterilized for use in medical environments.

The ends of the fibers are easily accessed with the package by deflecting a flexible portion thereof. Fiber may be unwound from either end without removing all of the fiber from the package. The package may be hung from a supporting device so that it does not interfere with use of the fiber. The package may be easily relocated along the fiber as necessary.

SUMMARY OF THE INVENTION

The present invention includes a package for a flexible fiber comprising first and second package portions disposed adjacent to one another and defining a fiber receiving cavity therebetween. At least one of the package portions comprises flexible lip means for allowing insertion of the fiber between the first and second portions into the cavity.

In the preferred embodiment, the cavity is substantially annular. The first and second package portions are fixedly attached to one another radially inwardly of the cavity.

The flexible lip means may be an integral portion of one of the package portions, and in one embodiment, is characterized by an angled lip extending away from the other of the package portions. Both package portions may comprise such a flexible lip means facing one another such that a generally V-shaped perimeter channel is formed on which the fiber may be wound. The flexible lip means move apart so that the fiber may then pass into the fiber receiving cavity.

The present invention also includes a fiber package assembly comprising a package, defining a fiber receiving cavity therein and a fiber end receiving cavity in communication with the fiber receiving cavity, and a length of elastically flexible fiber coiled within the fiber receiving cavity and having an end extending into the fiber receiving cavity. Preferably, the fiber end receiving cavity extends substantially tangentially from the fiber receiving cavity.

The package further comprises a means, such as a flexible portion of the package, for allowing deflection of the fiber end receiving cavity away from the fiber end. The fiber end is thus freed from the fiber end receiving cavity, and the natural spring action of the coiled fiber will cause the fiber end to pop out in a substantially radially outward direction from the package.

In one embodiment, the fiber end receiving cavity is a first fiber end receiving cavity, and the fiber end is a first fiber end. The package may further define a second fiber end receiving cavity in communication with the fiber receiving cavity. A second end of the fiber may be positioned so that it extends into the second fiber end receiving cavity.

One method of use of the invention comprises the steps of deflecting a portion of a package in which a length of fiber is wound or spooled such that a first end of the fiber pops out of the package by natural spring action of the fiber, and unwinding a portion of the fiber from the package by pulling on the first end. The method may further comprise the steps of deflecting another portion of the package such that a second end of the fiber pops out of the package by the natural spring action of the fiber, and unwinding another portion of the fiber from the package by pulling on the second end. The method may additionally comprise rewinding the fiber onto the package.

The invention further includes a method for repositioning a package with ends of fibers extending therefrom by rolling the package along the fiber such that one portion of the fiber is rewound onto the package and the other portion of the fiber is further unwound from the package.

The invention may also be described as an apparatus comprising a package defining a cavity therein with a substantially coiled fiber disposed in the cavity. The fiber comprises a first end extending a first length from the package and a second end extending a second length from the package, the first and second lengths defining a total length of fiber extending from the package. The apparatus further comprises means for repositioning the package between the first and second ends while maintaining the total length substantially constant. The means for repositioning may comprise a flexible portion of at least one of first and second package portions whereby the first and second lengths of fiber are free to pass between the first and second package portions as the package is rotated about a central axis thereof. As one of the first and second lengths of the fiber is unwound from the cavity in the package, the other of the first and second lengths of fiber is rewound into the cavity in the package.

The present invention is particularly adapted for fiber optics applications wherein the fiber is a light transmitting fiber. In particular, but not by way of limitation, the invention may be used in medical areas in which the fiber is a surgical laser light transmitting fiber. The package readily lends itself to sterilization prior to use. The package and fiber are easily used without unwinding unnecessary portions of the fiber from the package which avoids complications during use. After use, the fiber may be rewound onto the package so that the package and fiber may be easily discarded as biomedical waste.

Numerous objects and advantages of the invention will become apparent as the following detailed description of the preferred embodiments is read in conjunction with the drawings which illustrate such embodiments.

BRIEF DESCRIPTION OF THE DRAWINGS

FIG. 1 shows a side elevational view of the fiber package of the present invention.

FIG. 2 presents a partial edge elevation and cross section taken along lines 2—2 in FIG. 1.

FIG. 2A is an enlargement of a portion of FIG. 2 illustrating how a fiber may be wound onto or unwound from the package.

FIG. 3 is a top end view with a partial cross section taken along lines 3—3 of FIG. 1.

FIG. 3A is an enlarged portion of FIG. 3 illustrating how a portion of the package may be deflected so that a fiber end will automatically pop out of the package. The lower portion of FIG. 3A is taken along lines 3—3 in FIG. 1, and the upper portion of FIG. 3A is taken along lines 3'—3' in FIG. 1.

FIG. 4 is a partial elevation and cross section taken along lines 4—4 in FIG. 1.

DESCRIPTION OF THE PREFERRED EMBODIMENT

Figure 5:
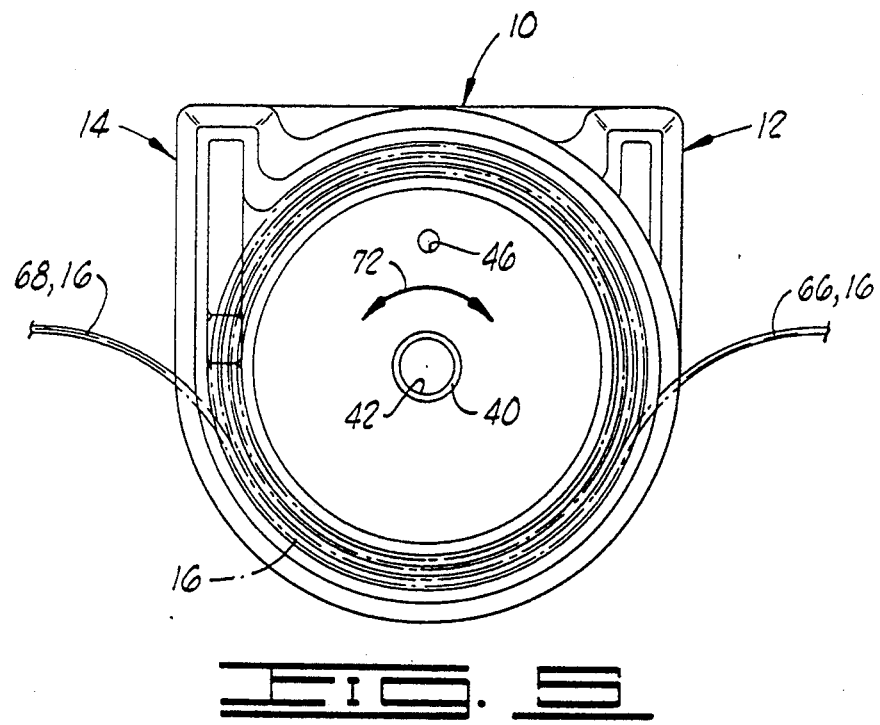
FIG. 5 illustrates how the package may be repositioned along a length of the fiber.

Referring now to the drawings, and more particularly to FIGS. 1 and 2, the package for an elongated flexible fiber of the present invention is shown and generally designated by the numeral 10. Package 10 generally comprises a first package portion 12 attached to a second package portion 14. In one embodiment, but not by way of limitation, first and second portions 12 and 14 are substantially identical. Package 10 is adapted for receiving a length of fiber 16 which is wound, as on a spool, into package 10, as will be further discussed herein.

The details of first package portion 12 will be discussed, but it should be understood that the details of second package portion 14 in the illustrated embodiment are substantially the same. Package portion 12 is mostly of circular configuration having a radially outer lip 18. Lip 18 is substantially annular. Extending tangentially to lip 18 are a pair of substantially perpendicular edges 20 and 22 of a generally square corner portion 24.

As seen in FIG. 2, first and second package portions 12 and 14 touch one another and are connected along a plane 26 defined between the two package portions. A central axis of first and second package portions 12 and 14 will be seen to be perpendicular to plane 26. Lip 18 extends radially outwardly with respect to the central axis and away from plane 26. First package portion 12 has a substantially annular shoulder 28 adjacent to lip 18, and this shoulder is normally in contact with a corresponding shoulder on second package portion 14. A substantially annular groove 30 is defined radially inwardly from shoulder 28 and faces a similar annular groove in second package portion 14. As will be further discussed herein, the two grooves 30 define a fiber-receiving cavity 31 in package 10.

Another annular shoulder 34 is disposed radially inwardly of groove 30. Shoulder 34 is in contact with, and is fixedly attached to, a corresponding shoulder on second package portion 14. Any fastening means of a kind known in the art may be used to connect shoulders 34, such as heat bonding, rivets, adhesives, etc. Referring to FIG. 2A, another embodiment of the fastening means is shown. In this embodiment, first package portion 12 has a male snap portion 32 thereon, and second package portion has a corresponding female snap portion 33. Female snap portion 33 is adapted to grippingly receive male snap portion 32 so that first and second package portions 12 and 14 are adequately held together. A plurality of such male and female snap portions 32 and 33 may be disposed around annular shoulders 34. Obviously, in the embodiment utilizing male and female snap portions 32 and 33, first and second package portions 12 and 14 are not exactly identical. However, in the preferred embodiment, all but male and female snap portions 32 and 33 of first and second package portions 12 and 14 are the same.

Radially inwardly of shoulder 34 is a substantially circular recess 36 which faces a corresponding recess in second package portion 14. Recesses 36 together form a label-receiving cavity 37 in which is disposed a label 38. Label 38 can carry marketing and instructional information, as desired. When label 38 is disposed in package 10, it is preferable that at least a portion of package 10 be substantially transparent. It will be seen that once shoulders 34 are affixed to one another, label 38 is totally retained within package 10.

At the center of first package portion 12 is a tubular portion 40 with a central opening 42 defined therethrough. A corresponding tubular portion 40 extends from second package portion 14 and is aligned therewith. A hole 44 is defined in the center of label 38 and may be considered a portion of central opening 42. Tubular portion 40 and central opening 42 are located on the central axis of package 10.

Spaced from central opening 42 is an opening 46 defined through first and second package portions 12 or 14 and also through label 38. As will be further discussed herein, opening 46 is used to hang package 10 and any fiber 16 contained therein from a hook or other known means. Preferably, opening 46 is spaced above a center of gravity of package 10 and fiber 16.

If openings 46 are formed before assembly, they can be used to align the various components of package 10 during assembly thereof. If openings 46 are punched through an assembled package 10, an extruded portion 47 of one of said first and second package portions 12 and 14 adjacent to opening 46 therein may extend through opening 46 in the other of the first and second package portions. See FIG. 2A. This extruded portion 47 provides a locking means for preventing relative rotation between first and second package portions 12 and 14. Snap portions 32 and 33 may also provide such a locking means.

Referring now also to FIGS. 3 and 4, square corner portion 24 defines an elongated cavity 48 which extends tangentially from groove 30 and is in communication therewith. As will be further discussed herein, cavity 48 may be referred to as a fiber end receiving cavity 48 or a terminal receiving cavity 48. A tapered surface 50 provides a somewhat gradual transition between groove 30 and the major portion of cavity 48, as best seen in FIG. 4.

With regard to FIG. 1, cavity 48 in first package portion 12 opens away from the page, and cavity 48 in second package portion 14 opens toward the page. Thus, it will be seen that a portion of cavity 48 in each package portion is exposed and another portion of cavity 48 is covered by the other package portion. If viewing the opposite side as shown in FIG. 1, package 10 will look the same as in FIG. 1.

A shoulder 52 is defined around cavity 48. Shoulder 52 normally lies in plane 26, and it will be seen that shoulder 52 extends from shoulder 28 which also lies in plane 26.

An angled lip 53 extends away from shoulder 52. It will be seen that lip 53 is an extension of lip 18.

Referring now to FIGS. 2 and 2A, it will be seen that lips 18 on first and second package portions 12 and 14, define a generally V-shaped perimeter groove 54. It will be seen that half of groove 54 is interrupted adjacent to each cavity 48.

Forming part of the boundary of each groove 30, and thus of fiber-receiving cavity 31 is a radially inner wall 56 adjacent to shoulder 54.

Flexible fiber 16 may be positioned in fiber-receiving cavity 31 in the following manner. A portion of fiber 16 is wrapped onto package 10 in groove 54. First and second package portions 12 and 14 are preferably made of flexible material so that when a little pressure is applied to fiber 16, flexible lips 18 and shoulders 28 will be pushed apart so that the fiber may be passed through a gap 58 defined therebetween. Fiber 16 may be then wrapped around walls 56 which act as a spool means for receiving the length of fiber 16 wrapped therearound.

Fiber 16 may be completely enclosed in fiber-receiving cavity 31 by continuing to wrap the fiber as described.

In the preferred embodiment, one end of fiber 16 is positioned so that it extends into fiber end cavity 48 in first package portion 12, and the other end of fiber 16 is positioned so that it extends into fiber end receiving cavity 48 in second package portion 14. The natural spring action of fiber 16 will generally cause it to expand outwardly toward radially outer wall 60 which forms a part of groove 30. Wall 60 is preferably substantially perpendicular to plane 26 between first and second package portions 12, so the fiber will not force itself back out between shoulder 28 and lips 18. That is, once the fiber is wrapped within package 10, it will remain in place with the ends of fibers extending into fiber end receiving cavities 48 and the remainder of the coiled fiber in fiber-receiving cavity 31.

Fiber 16 may be of any type of fiber generally having some elastic resiliency or "natural spring action" as defined previously herein. In one embodiment, although it is not intended that the invention be so limited, the fiber is of the type used in fiber-optic systems. That is, fiber 16 is a light-transmitting fiber. Typically for such usage, one end of the fiber has a terminal 62 on one end thereof which is adapted for connecting to a light source. Such a terminal 62 is shown in terminal-receiving cavity 48 of first package portion 12 in FIGS. 3, 3A and 4. The other end of fiber 16 in such applications typically has another device, such as an operating tip 63 thereon which utilizes the light transmitted through the fiber and further transmits the light to another location. Such an operating tip 63 is illustrated in terminal receiving cavity 48 of second package portion 14 in FIG. 1.

For example, but not by way of limitation, fiber 16 may be a light-transmitting fiber adapted for connection to a surgical laser. Terminal 62 may be adapted for connection to such a laser and the other end of fiber 16 could contain a surgical operating tip 63 utilizing the laser light for performing a surgical procedure on a patient. In such cases, package 10 and fiber 16 may be readily sterilized together and maintained in a sterile condition until ready for use.

In gaining access to fiber 16 within package 10, the following procedure is preferred. Referring now to FIGS. 3 and 3A, lip 53 adjacent to shoulder 52 running alongside fiber end receiving cavity 48 of one of first package portion 12 is deflected away from the second package portion 14. To facilitate proper deflection of lip 53 in this corner portion 24, an indicator means is provided on lip 53 for indicating an approximate location for applying the force necessary for the deflection. As illustrated in FIG. 1, this indicator means may be characterized by an instruction, such as the word "PRESS" and/or an arrow 80 This indicator means may be imprinted on lip 53. "Imprinted" for the purposes of this disclosure can include actual printing on lip 53, molding the words or arrow therein, or any other means of affixing instructions or arrow 80. It is not intended that the invention be limited to the precise location of the indicator means as illustrated in FIG. 1.

As shown in FIG. 3A, corner portion 24, including lip 53 and shoulder 52, of first package portion 12 are shown deflected away from second packing portion 14. As previously indicated, shoulders 34 are fixedly attached to one another so that square corner portion 24 is substantially moved away such that a gap 64 is defined between shoulder 52 and second package portion 14. When gap 64 is sufficiently large, terminal 62 will be free to pass therethrough. As gap 64 reaches this size, the natural spring action of coiled fiber 16 will cause terminal 62 and a section 66 of fiber 16 to pop out of cavity 48 in a generally radially outward direction as seen in FIG. 3A.

Section 66 may be extended further from package 10 by simply pulling thereon and allowing the package 10 to rotate about central opening 42. For example, but not by way of limitation, opening 42 may be sized so that an operator can place a finger therethrough and simply allow the package to rotate on that finger as section 66 is pulled out further.

After terminal 62 and the corresponding end of fiber 16 are thus freed from package 10, terminal 62 may be connected to a light source or other device as desired.

The other end of fiber 16 may also be freed from cavity 48 in second package portion 14 in a substantially identical manner to that described previously. That is, corner portion 24 of second package portion 14 may be deflected away from first package portion 12 such that operating tip 63 and a second section 68 of fiber 18 will pop out of package 10 due to the natural spring action of coiled fiber 16. This is illustrated in FIG. 1.

Referring now to FIG. 5, first and second sections 66 and 68 of fiber 16 are shown released from package 10 and extending therefrom. Only the amount of fiber 16 that is actually necessary need be unwound from package 10. Assuming that some portion of fiber 16 remains in fiber-receiving cavity 31, package 10 may be repositioned along the extended fiber 16 by simply rolling it along the fiber in the direction desired as indicated by arrows 72 in FIG. 5. For example, package 10 may be rotated in a clockwise direction toward first fiber section 66. As this occurs, section 66 is wound back onto package 10 and into fiber-receiving cavity 31 while second fiber section 68 is further unwound from package 10. If package 10 is rotated in a counterclockwise direction, second section 68 is wound into fiber-receiving cavity 31, while first section 66 is further unwound therefrom. It will be seen by those skilled in the art that package 10 thus may be positioned anywhere along the extended length of fiber 16 without changing the total amount of fiber extended from the package.

Figure 6:
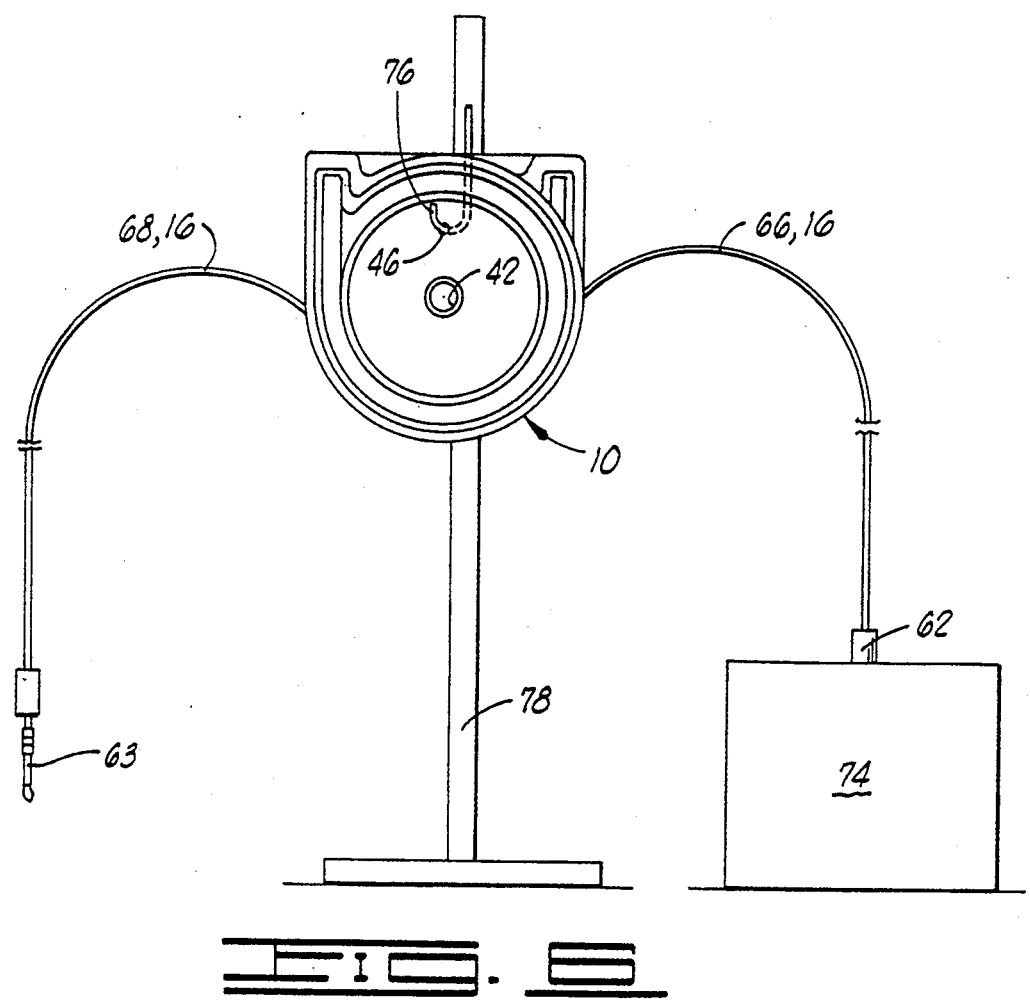
FIG. 6 illustrates the package and fiber in use, as in a medical environment.

Referring now to FIG. 6, package 10 is shown with first and second fiber sections 66 and 68 extending therefrom. Terminal 62 is connected to a light source such as a laser 74. Operating tip 63 is ready for use. Package 10 may be hung from any supporting device, such as a hook 76 on an IV stand 78 in a surgical operating environment by extending the hook through hole 46. Because hole 46 is positioned above the center of gravity of package 10 and fiber 16, it will hang downwardly in a neat manner without entangling fiber sections 66 or 68.

After usage, first and second sections 66 and 68 of fiber 16 may be rewound onto package 10 in the manner previously described. Terminal 62 and operating tip 63 may be repositioned within the corresponding fiber end receiving cavities 48 in first and second package portions 12 and 14, so that basically the entire assembly of package 10 and fiber 16 is in the same configuration as it was originally.

In some applications, the entire apparatus may be reused. In applications such as surgical lasers, it will be seen that the package may be easily disposed of as biomedical waste. Because fiber 16 is rewound into fiber-receiving cavity 31 in package 10, the package is returned to a compact configuration and there is no problem with trying to handle contaminated fibers which may become entangled and cause problems in disposal.

It will be seen, therefore, that the package for an elongated flexible fiber of the present invention is well adapted to carry out the ends and advantages mentioned as well as those inherent therein. While presently preferred embodiments of the apparatus and methods of use have been described for the purposes of this disclosure, numerous changes in the arrangement of parts and methodological steps may be made by those skilled in the art. All such changes are encompassed within the scope and spirit of the appended claims.

What is claimed is:

1. A method of utilizing a length of fiber spooled in a package, said method comprising the steps of:
    deflecting a first flexible portion of said package away from another portion of said package such that a gap is formed between said portions of said package and a first end of said fiber pops out of said package by natural spring action of said fiber; and
    unwinding a portion of said fiber from said package by pulling on said first end.

2. The method of claim 1 further comprising the step of rewinding said fiber onto said package.

3. The method of claim 1 further comprising the step of hanging said package from a supporting device at a position on said package spaced above a center of gravity of said package.

4. The method of claim 1 further comprising supporting said package at a center finger hole while unwinding said fiber from said package.

5. The method of claim 1 wherein said fiber is a light-transmitting fiber with a terminal attached to said first end; and
    further comprising the step of attaching said terminal to a light source.

6. The method of claim 1 further comprising the steps of:
    deflecting a second flexible portion of said package such that another gap is formed and a second end of said fiber pops out of said package by natural spring action of said fiber; and
    unwinding another portion of said fiber from said package by pulling on said second end.

7. The method of claim 6 further comprising the step of repositioning said package by rolling said package along said fiber such that one of said portions of said fiber is rewound onto said package and the other of said portions of said fiber is further unwound from said package.

8. The method of claim 6 wherein:
    said fiber is a surgical laser-transmitting fiber;
    said fiber has a laser connector attached to said first end of said fiber;
    said fiber further has an operating tip attached to said second end of said fiber; and
    further comprising the step of attaching said laser connector to a laser.

9. The method of claim 8 further comprising:
    disconnecting said connector from said laser and rewinding said fiber onto said package; and
    disposing of said package and fiber therein as biomedical waste.

10. The method of claim 1 further comprising, prior to the other steps, sterilizing said fiber and package.

11. A package for holding and dispensing a length of fiber, said package comprising:

a first package portion defining an annular groove therein, said first package portion comprising:

a deflectable corner portion defining a cavity extending tangentially with respect to said groove and in communication therewith;

an annular lip disposed substantially around said groove;

a corner lip disposed on said corner portion adjacent to said cavity, said corner lip being an extension of said annular lip; and an attaching shoulder; and a second package portion substantially identical to said first package portion and affixed to said first package portion along a plane defined by the attaching shoulders thereof such that the grooves form a fiber-receiving cavity; wherein:

the corner portion of each of said first and second package portions is deflectable away from said plane; and a portion of said cavity in said deflectable corner portion of said first package portion is exposed and another portion of said cavity in said deflectable corner portion of said first package portion is covered by said second package portion.

12. The package of claim 11 wherein said attaching shoulders are radially inwardly of said grooves.

13. The package of claims 11 wherein the annular lips are radially outwardly of the groove.

14. The package of claim 11 wherein said first and second package portions are made of a flexible material such that the annular lips may be deflected away from one another.

15. The package of claim 11 wherein said first and second package portions are made of a flexible material adjacent to said corner portion defining said cavity.

16. The package of claim 11 further comprising indicator means for indicating an approximate location on said corner portion for applying a force for deflecting said corner portion away from said plane.

17. The package of claim 16 wherein said indicator means comprises an instruction imprinted on said corner portion.

18. The package of claim 16 wherein said indicator means comprises an indicator arrow imprinted on said corner portion.

19. The package of claim 11 wherein said package is sterile.

20. The package of claim 11 further comprising locking means for preventing relative rotation between said first package portion and said second package portion.

* * * * *